United States Patent [19]
Higo et al.

[11] Patent Number: 5,985,843
[45] Date of Patent: Nov. 16, 1999

[54] PHARMACEUTICAL COMPOSITION CONTAINING SUCRALFATE

[75] Inventors: Shoichi Higo; Kazuo Igusa, both of Tokyo, Japan

[73] Assignee: Chugai Seiyaku Kabushiki Kaisha, Tokyo, Japan

[21] Appl. No.: 08/930,263

[22] PCT Filed: Apr. 2, 1996

[86] PCT No.: PCT/JP96/00891

§ 371 Date: Sep. 26, 1997

§ 102(e) Date: Sep. 26, 1997

[87] PCT Pub. No.: WO96/31218

PCT Pub. Date: Oct. 10, 1996

[30] Foreign Application Priority Data

Apr. 3, 1995 [JP] Japan .................................. 7-077781

[51] Int. Cl.$^6$ ................................................. A61K 31/715
[52] U.S. Cl. .............................................. 514/25; 514/27
[58] Field of Search ........................................ 514/25, 27

[56] References Cited

U.S. PATENT DOCUMENTS

| 5,260,304 | 11/1993 | Gergely et al. | 514/58 |
| 5,593,696 | 1/1997 | McNally et al. | 424/472 |

FOREIGN PATENT DOCUMENTS

| 50-53521 | 5/1975 | Japan | 514/58 |
| 1-128925 | 5/1989 | Japan | 514/58 |
| 3-24020 | 12/1991 | Japan | 514/58 |
| 6-502855 | 3/1994 | Japan | 514/58 |

*Primary Examiner*—James H. Reamer
*Attorney, Agent, or Firm*—Browdy and Neimark

[57] ABSTRACT

Disclosed is a pharmaceutical preparation that contains sucralfate is the presence of another drug and which consists of a delayed release fraction of sucralfate and an immediate release fraction of the another drug. The preparation exhibits an outstanding feature such that when administered, the drug coexistent with the sucralfate can maintain its inherent absorption characteristics without being adsorbed, trapped or otherwise affected by the sucralfate.

13 Claims, 4 Drawing Sheets

PHARMACEUTICAL COMPOSITION CONTAINING SUCRALFATE

TECHNICAL FIELD

This invention relates to pharmaceutical preparations that contain drugs in combination with sucralfate and which permit the drugs to maintain their inherent absorption characteristics without being adsorbed on or trapped by the sucralfate.

BACKGROUND ART

Sucralfate in the digestive tract reacts with gastric acid to form a bio-adhesive gel which adheres to the mucous membrane of the digestive tract, thereby creating a local protective barrier. At the inflammatory or ulcer site, the protective barrier protects the mucous membrane of the digestive tract from excessive gastric acid and the like and promotes the ability of the human body to repair the mucous membrane of the stomach, thereby exhibiting a healing effect. In expectation of its ability to protect the mucous membrane of the stomach, sucralfate is administered simultaneously with various drugs at the medical setting.

However, depending on the drug to be administered simultaneously with sucralfate, the bio-adhesive gel composition formed of the sucralfate will adsorb the drug, trap it within the gel composition, form a complex or be subject to other adverse effects that either prevent or retard the absorption of the drug itself. To mention a few examples of the cases that have been reported on these phenomena, Brouwers et al. reported in 1990 that Tmax, Cmax, AUC and bio-availability of ciprofloxacin dropped significantly when used in combination with sucralfate (Drug Invest., 2(3):197, 1990); in the same year, Lafontaine et al. reported delayed absorption of naproxen due to simultaneous administration of sucralfate (Clin. Pharm., 9(10):773, 1990); Cantral et al. reported reduced AUC of theophylline due to sucralfate (Clin. Pharm., 7(1):58, 1988); Anaya et al. reported delayed absorption of ibuprofen due to simultaneous administration of sucralfate (Biopharm. Drug Dispos., 7(5):443, 1986); Maconochie et al. reported reduced AUC and Cmax levels of ranitidine due to simultaneous administration of sucralfate (Clin. Pharmacol. Ther., 41(2):205, 1987); and Yoshida et al. reported reduced AUC of cimetidine due to simultaneous administration of sucralfate (Journal of the Society of Gastrointestinal Diseases of Japan, 84(5):1025, 1987).

The beecham Group Public Limited Company filed Japanese Patent Application No. 500445/1992, in which they took advantage of the adsorptive action of sucralfate in ensuring the local sustained release of $H_2$ antagonists.

Although it is known that when sucralfate is incorporated or administered simultaneously with other drugs, it adsorbs, traps or otherwise affects the drugs to potentially interfere with their absorption, few proposals have been made offering effective methods and means for avoiding the problem. In the actual medical setting, some provisions are necessary such as the avoidance of combined use of sucralfate and other drugs or sequential administration of the two drugs with a certain time interval being allowed; thus, it has been difficult to secure the high bioavailability of drugs when they are administered simultaneously with sucralfate.

DISCLOSURE OF INVENTION

An object, therefore, of the present invention is to provide a pharmaceutical preparation that contain sucralfate in the presence of another drug and which eliminates the adverse effects of the sucralfate on the another drug so as to secure its inherent bioavailability.

Under the circumstances described above, the present inventors conducted intensive studies in order to provide a pharmaceutical preparation that contained sucralfate in the presence of another drug and which could prevent the sucralfate from interfering with the absorption of the other drug. As a result, they found that a pharmaceutical preparation consisting of an immediate release fraction and a delayed release fraction, with sucralfate forming the delayed release fraction and another drug the immediate release fraction, could effectively maintain the intended absorption characteristics of the drug without being adsorbed, trapped or otherwise affected by the sucralfate.

Figure 1:
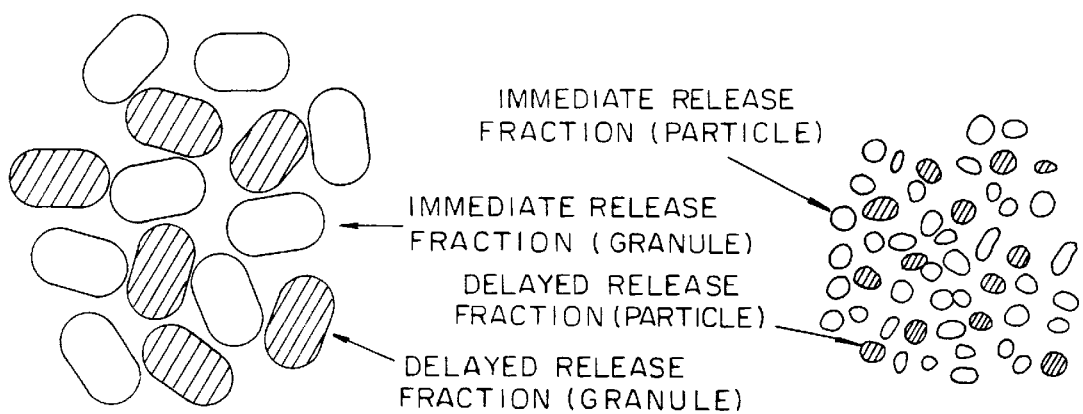
FIG. 1 illustrates a bigranular mixed pharmaceutical preparation according to the invention in which an immediate-release fraction of granules is mixed with a delayed-release fraction of granules, as well as a biparticulate mixed pharmaceutical preparation according to the same invention.
Figure 2:
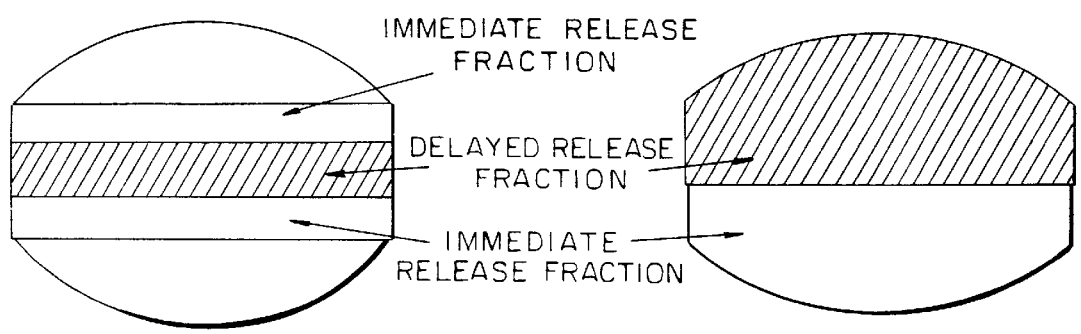
FIG. 2 illustrates a two-layer tablet according to the invention which consists of an immediate-release layer and a delayed-release layer, as well as a three-layer tablet according to the same invention.
Figure 3:
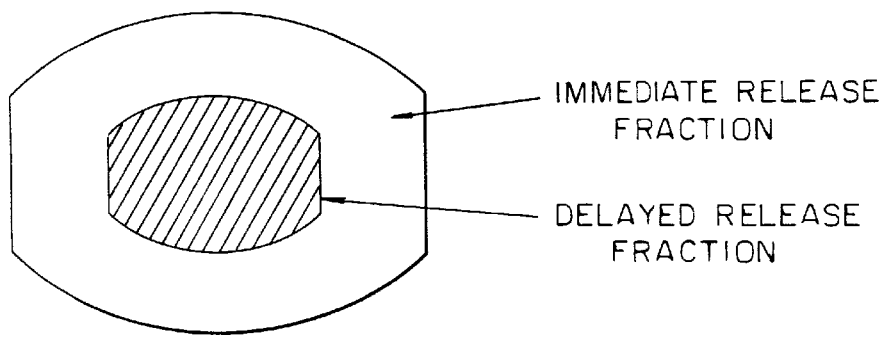
FIG. 3 illustrates a tablet according to the invention which consists of a delayed release core surrounded by an immediate release shell.
Figure 4:
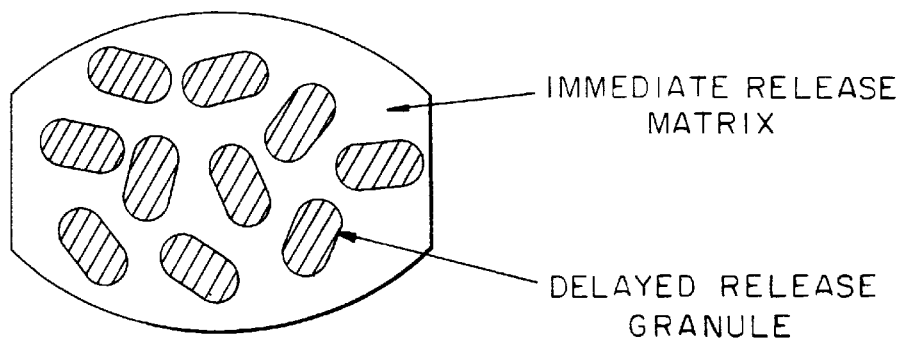
FIG. 4 illustrates a tablet according to the invention which comprises an immediate release matrix having delayed-release granules dispersed therein.
Figure 5:
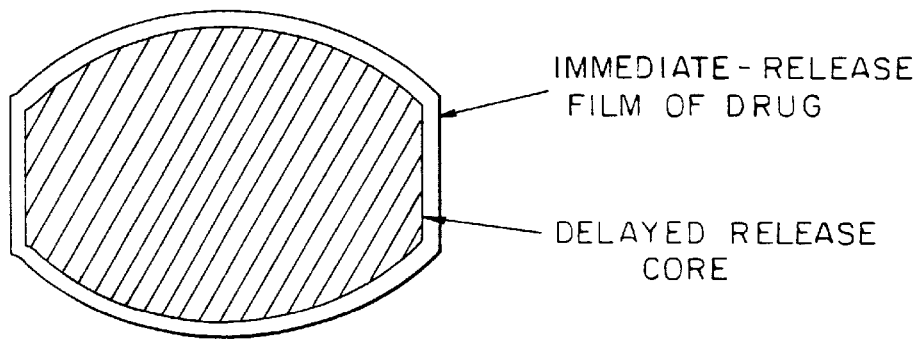
FIG. 5 illustrates a tablet consisting of a delayed-release core coated with an immediate-release film of a drug.
Figure 6:
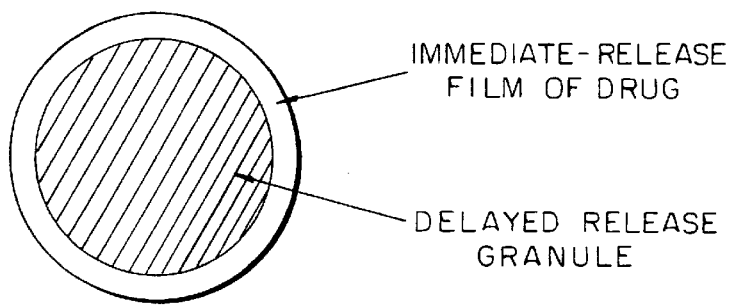
FIG. 6 illustrates a granular pharmaceutical preparation consisting of a delayed-release core granule coated with an immediate-release film of drug.
Figure 7:
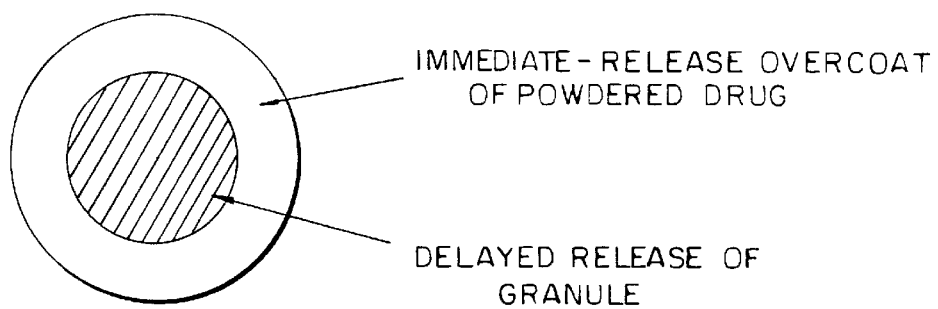
FIG. 7 illustrates a granular pharmaceutical preparation consisting of a delayed-release core granule coated with an immediate-release layer of powdered drug.
Figure 8:
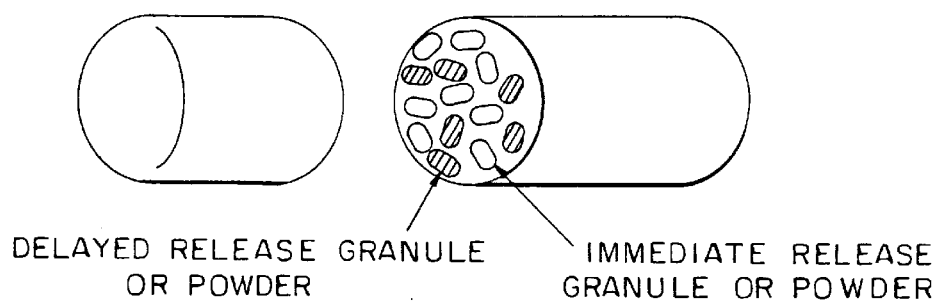
FIG. 8 illustrates a capsule filled with a mixture comprising a delayed-release tablet, granule or powder combined with an immediate-release tablet, granule or powder.

The invention provides a pharmaceutical preparation containing sucralfate as a delayed release fraction and another drug as an immediate-release fraction such that the drug forming the immediate-release fraction is rapidly disintegrated and released, followed by delayed disintegration and release of the sucralfate forming the delayed release fraction. The drug first disintegrated and released from the pharmaceutical preparation is immediately dissolved or dispersed in gastric juice and other liquid secretions in the human body and, hence, it is capable of transfer to the absorption site without being adsorbed, trapped or otherwise affected by the sucralfate which later disintegrates to form a gel by reaction with gastric acid.

In the pharmaceutical preparation of the present invention, the component to be contained as the delayed release fraction is limited to sucralfate; however, the techniques and additives that are to be applied to the delayed release fraction for achieving delayed disintegration, or the techniques and additives that are to be applied to the immediate release fraction for achieving accelerated disintegration are in no way limited in terms of type and the amount of incorporation.

For example, pharmaceutical formulation techniques that may be employed to provide the slow release fraction include the addition of oleaginous bases such as hardened oils and waxes typified by fatty acids, gel-forming bases such as water-soluble polymers typified by cellulosic derivatives such as methyl cellulose, hydroxypropyl cellulose and hydroxypropyl methyl cellulose, and matrix bases typified by hydrophobic bases such as ethyl cellulose and acrylic acid copolymers, as well as coating with films of the aforementioned water-soluble polymers, etc. Methods for obtaining the immediate release fraction include the addition of effervescent bases exemplified by sodium bicarbonate and citric acid, and the addition of disintegrants including starch derivaties such as partial alphaconverted starch, carboxymethyl starch sodium and hydroxypropyl starch, and cellulosic derivatives such as carmellose, carmellose calcium, cross-carmellose sodium and low-substitution hydroxypropyl cellulose. Possible pharmaceutical formulation techniques include freeze drying and fluidized bed granulation. The present invention also is not limited in terms of the internal layout and dosage form of the immediate and delayed release fractions.

The drugs that may be used in the invention in combination with sucralfate are those which will be adsorbed, trapped or otherwise affected by the sucralfate to be prevented from efficient absorption and include the following: antiepileptics such as diazepam and phenytoin; antipyretics and analgesics such as acetaminophen, aspirin, ibuprofen ketoprofen, naproxen and indomethacin; psychopharmacologic agents such as chlorpromazine hydrochloride, imipramine hydrochloride and sulpiride; antispasmodic drugs such as methyl bromide methylbenactyzium bromide; cardiotonics such as digoxin; antidysrhythmic drugs such as procainamide hydrochloride, indenolol hydrochloride and verapamil hydrochloride; diuretics such as furosemide; hypotensive drugs such as nicardipine hydrochloride; coronary vasodilators such as diltiazem hydrochloride, dipyridamole and nifedipine; bronchodilators such as theophylline; $H_2$-receptor antagonists such as cimetidine, ranitidine, famotidine, nizatidine and loxatidine acetate; hormones such as prednisolone, ethynyl estradiol and warfarin potassium; antidiabetic drugs such as chlorpropamide; and antibacterials such as aluminoparaaminosalicylic acid calcium salt, erythromycin, ciprofloxacin hydrochloride and norfloxacin; preferred examples are $H_2$-receptor antagonists such as cimetidine, ranitidine, famotidine, nizatidine and loxatidine acetate. Two or more of the drugs listed above may be used in appropriate combinations.

Following are typical examples of the dosage form with which the present invention may be implemented but it should be noted that other structures may be adopted as long as they provide dosage forms that permit the present invention to be implemented.

(1) a bigranular or biparticulate mixed pharmaceutical preparation manufactured by mixing an immediate release fraction of granules with a delayed release fraction of granules;
(2) a two- or three-layered tablet comprising an immediate release layer and a delayed-release layer;
(3) a tablet consisting of a delayed release core surrounded by an immediate release shell;
(4) a tablet comprising an immediate release matrix having delayed release granules dispersed therein;
(5) a tablet comprising a delayed release core coated with an immediate-release film of drug;
(6) a granular phamaceutical preparation comprising a delayed release core granule coated with an immediate-release film of drug;
(7) a granular pharmaceutical preparation comprising a delayed release core granule coated with an immediate-release layer of powdered drug;
(8) a capsule filled with a mixture comprising a delayed release tablet, granule or powder combined with an immediate release tablet, granule or powder; and
(9) a solution (or jelly) having delayed release particles dispersed in an aqueous solution (or jelly) of drug.

The amount of sucralfate to form the delayed release fraction of the pharmaceutical composition of the invention is not limited to any particular value; in terms of single dose, 300–1,200 mg which is common for sucralfate is desired and the range of 500–1,080 mg is preferred. The amount of the drug to form the immediate release fraction of the pharmaceutical composition also is not limited to any particular value and the amount with which the normal efficacy can be expected is desired.

The following examples are provided for the purpose of further illustrating the present invention but it should be understood that the invention is by no means limited by the pharmaceutical preparations set forth below.

EXAMPLE 1

| (Bigranular mixed preparation) | | |
|---|---|---|
| Delayed release granules | Sucralfate | 1,500 g |
| | D-Mannitol | 130 g |
| | Hydroxypropyl methyl cellulose | 60 g |

Sucralfate and D-mannitol were weighed, mixed, kneaded with the 10% ethanol and passed through a screen to form granules, which were dried and coated with hydroxypropyl methyl cellulose.

| Immediate release granules | Cimetidine | 400 g |
|---|---|---|
| | Lactose | 800 g |

Cimetidine and lacotse were weighed, mixed, kneaded with the aid of water and passed through a screen to form granules which were then dried.

The two granulations were separately weighed and mixed in prescribed amounts to formulate a bigranular preparation.

EXAMPLE 2

| (Two-layered tablet) | | |
|---|---|---|
| Delayed release powder | Sucralfate | 1,000 g |
| | Polyethylene glycol 6000 | 1,000 g |
| | Magnesium stearate | 2 g |
| | Hydrous silicon dioxide | 4 g |

-continued

| (Two-layered tablet) | | |
|---|---|---|
| Immediate release powder | Famotidine | 10 g |
| | Crystalline cellulose | 300 g |
| | Polyethylene glycol 6000 | 25 g |

Each components of the delayed and immediate release powders were separately weighed, mixed and processed by direct compression to prepare two-layered tablets.

EXAMPLE 3

| (Two-layered tablet) | | |
|---|---|---|
| Delayed release fraction | Sucralfate | 1,500 g |
| | D-Mannitol | 187 g |
| | Hardened oil | 300 g |
| | Calcium silicate | 8 g |
| | Calcium stearate | 5 g |
| Immediate release fraction | Ranitidine hydrochloride | 84 g |
| | Carboxymethyl starch sodium | 240 g |
| | Anhydrous calcium phosphate | 669 g |
| | Hardened oil | 3 g |
| | Calcium stearate | 4 g |

Each components of the delayed and immediate release fractions of powder were separately weighed, mixed and processed by direct compression to prepare two-layered tablets.

EXAMPLE 4

| (Cored tablet) | | |
|---|---|---|
| Core | Sucralfate | 1,000 g |
| | Sucrose fatty acid ester (HLP = 15) | 460 g |
| | Magnesium stearate | 10 g |
| | Hydroxypropyl methyl cellulose | 30 g |
| Shell | Nizatidine | 150 g |
| | Lactose | 4,675 g |
| | Carmellose calcium | 100 g |
| | Hydroxypropyl cellulose | 50 g |
| | Magnesium stearate | 25 g |

Core: Sucralfate, sucrose fatty acid ester and magnesium stearate powders were weighed, mixed and processed by direct compression to make tablets each weighing 147 mg, which were then coated with hydroxypropyl methyl cellulose.

Shell: A mixture of nizatidine, lactose and carmellose calcium powders was granulated with a 70% ethanol solution of hydroxypropyl cellulose, dried, mixed with magnesium stearate and processed with a cored tablet making machine to prepare cored tablets each weighing 650 mg.

EXAMPLE 5

| (Coated tablet) | | |
|---|---|---|
| Core | Sucralfate | 1,000 g |
| | Polyethylene glycol 6000 | 583 g |
| | Precipitated silicic anhydride | 10 g |
| | Magnesium stearate | 7 g |
| Coating | Loxatidine acetate | 75 g |
| | Hydroxypropyl methyl cellulose | 80 g |
| | Propylene glycol | 20 g |
| | Titanium oxide | 5 g |

Cores each weighing 320 mg were made by direct compression. Then, the ingredients of the coating were dissolved and dispersed in isopropanol and applied to the cores to form a coating, which was verified to be comprised of the required amount of loxatidine acetate.

EXAMPLE 6

| (Coated Spherical granule) | | |
|---|---|---|
| Core | Sucralfate | 1,000 g |
| | Spherical granules (nonpareil) | 900 g |
| | Hydroxypropyl cellulose | 100 g |
| Coating | Famotidine | 10 g |
| | D-mannitol | 200 g |
| | Hydroxypropyl methyl cellulose | 15 g |
| | Propylene glycol | 5 g |

The spherical granules in a centrifugal fluidized coating granulator were sprayed with a predetermined amount of an aqueous hydroxypropyl cellulose solution while, at the same time, they were sprayed with a predetermined amount of sucralfate from an automatic powder sprayer, followed by drying. By repeating the spray/dry steps, the application of sucralfate was completed. Thereafter, a 50% alcohol solution of hydroxypropyl methyl cellulose and propylene glycol for making the coating layer was sprayed in a predetermined amount while, at the same time, a mixture of famotidine and D-mannitol powders was sprayed in a predetermined amount, followed by drying. By repeating the spray/dry steps, coated spherical granules were produced.

EXAMPLE 7

| (Two-layered tablet) | | |
|---|---|---|
| Delayed release fraction | Sucralfate | 2,000 g |
| | Hydroxymethyl cellulose | 180 g |
| | Magnesium stearate | 20 g |
| Immediate release fraction | Methylbenactzium bromide | 40 g |
| | Hydroxypropyl starch | 100 g |
| | Calcium citrate | 2,040 g |
| | Magnesium stearate | 20 g |

Each components of the powders for the slow and immediate release fractions were separately weighed, mixed and processed by direct compression to make two-layered tablets.

COMPARATIVE EXAMPLE 1

| | (Granule) | |
|---|---|---|
| Ingredients | Sucralfate | 1,500 g |
| | Cimetidine | 400 g |
| | Mannitol | 237.5 g |
| | Lactose | 237.5 g |

The powders of the respective ingredients were weighed, mixed, kneaded with the 10% ethanol and forced through a screen to form a granulation, which was dried to make granules.

COMPARATIVE EXAMPLE 2

| | (Tablet) | |
|---|---|---|
| Ingredients | Sucralfate | 1,000 g |
| | Famotidine | 10 g |
| | Crystalline cellulose | 600 g |
| | Polyethylene glycol 6000 | 460 g |
| | Magnesium stearate | 2 g |
| | Hydrous silicon dioxide | 4 g |

The powders of the respective ingredients were weighed, mixed and processed by direct compression to make tablets.

Test Examples

Figure 9:
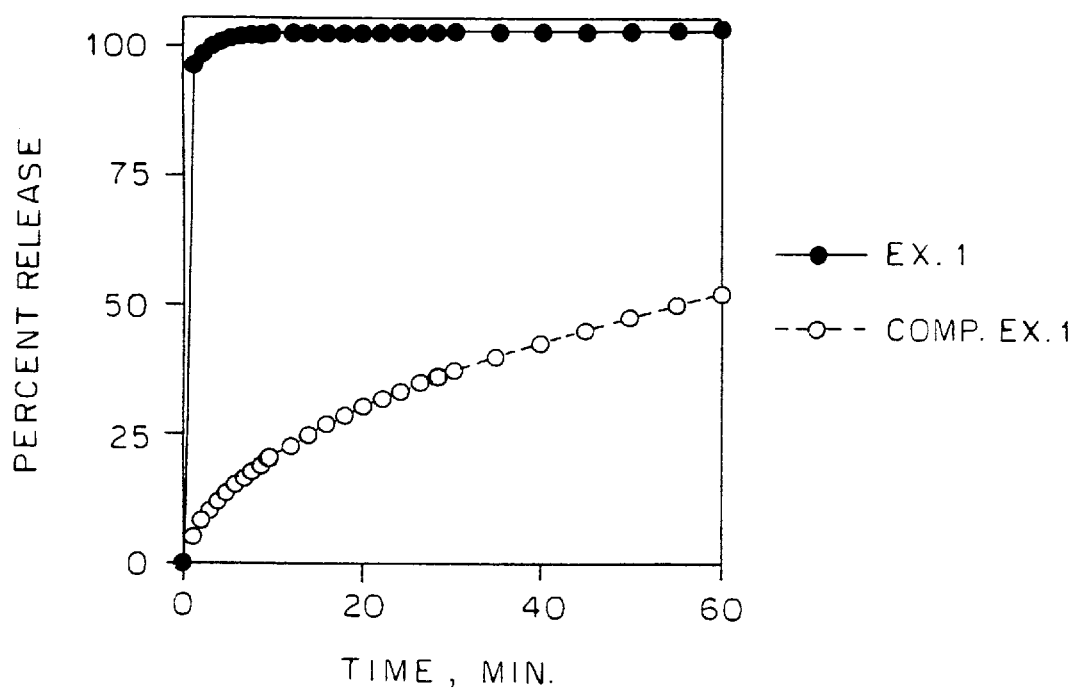
FIG. 9 is a graph showing the release curves of cimetidine in the granular pharmaceutical preparations of Example 1 of the invention and Comparative Example 1.

The bigranular mixed preparation of Example 1 was sampled out in an amount of 1927 mg (consisting of 800 mg of the immediate release fraction and 1127 mg of the delayed release fraction), as well as 1583 mg of the granules prepared in Comparative Example 1 were tested for dissolution by the rotary basket method described in the Japanese Pharmacopeia (JP) using 900 ml of the JP first fluid. Cimetidine was immediately released from the granules of Example 1 and 5–10 minutes later, sucralfate formed an adhering paste. In Comparative Example 1, sucralfate soon formed a paste, causing a delay of more than 50 min in the time required for the cimetidine to be released by 50% (see FIG. 9); thus, it was quantitatively confirmed that the drug cimetidine remained in the paste. The result of a JP disintegration test in water is shown in the table below.

Figure 10:
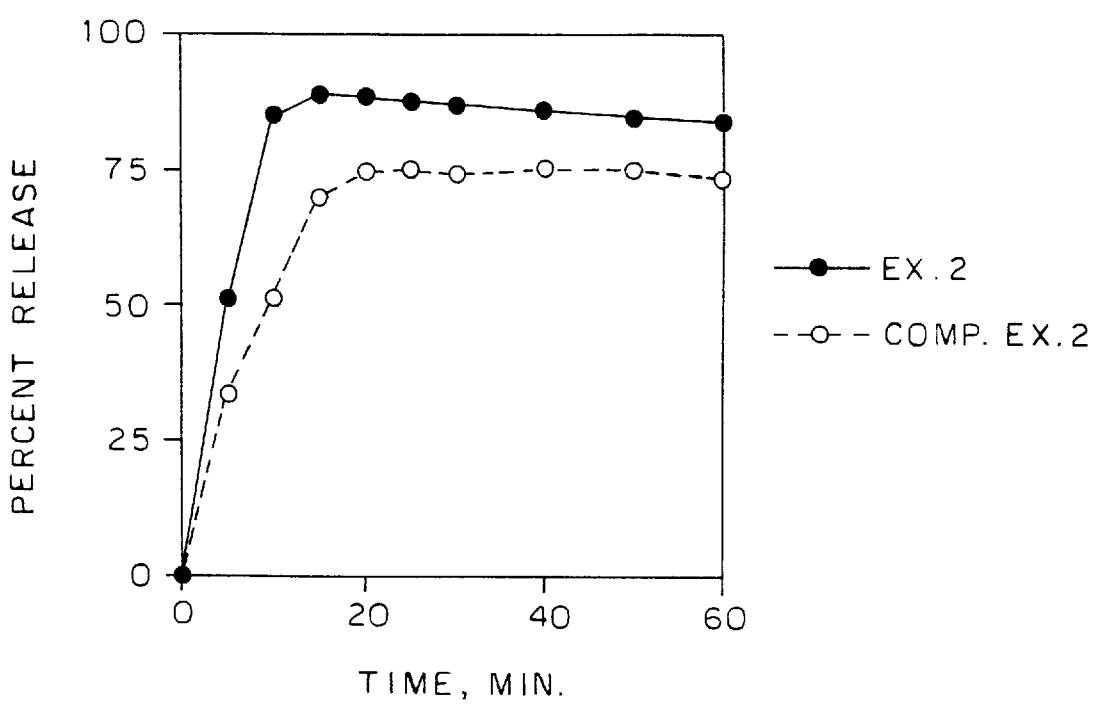
FIG. 10 is a graph showing the release curves of famotidine in the tablets of Example 2 of the invention and Comparative Example 2.

One of the tablets (585.3 mg) of Example 2 and one of the tablets (519 mg) of Comparative Example 2 were charged into 200 ml of the JP first fluid in beakers under stirring at 37° C. The supernatant was sampled at time intervals, filtered and subjected to absorbance measurement with a spectrophotometer. Famotidine was immediately released from the tablet of Example 2 and, thereafter, sucralfate formed an adherent paste. In Comparative Example 2, sucralfate soon formed a paste, causing a delay of more than 10 min in the time required for the famotidine to be released by 75% (see FIG. 10); thus, it was quantitatively confirmed that the drug famotidine remained in the paste. The result of a JP disintegration test in water is shown in the table below.

The same test was conducted on the preparations of Examples 3–7. The results of JP disintegration tests in water are also shown in the table below.

TABLE

Results of Disintegration Tests in Water

| Run No. | Disintegration (Dissolution) Time |
|---|---|
| Example 1 | 5 sec (immediate release granules) |
| | 8 min (delayed release granules) |
| Comparative Example 1 | 12 sec |
| Example 2 | 11 min (immediate release layer) |
| | 25 min (delayed release layer) |
| Comparative Example 2 | 9 min |
| Example 3 | 2 min (immediate release layer) |
| | 14 min (delayed release layer) |
| Example 4 | 1 min (shell) |
| | 16 min (core) |
| Example 5 | 3 min (coating layer dissolved) |
| | 14 min (core) |
| Example 6 | 4 min (coating layer dissolved) |
| | 15 min (core) |
| Example 7 | 2 min (immediate release layer) |
| | 15 min (delayed release layer) |

Industrial Applicability

Thus, according to the invention, pharmaceutical preparations containing both sucralfate and various other drugs can be produced that secure the inherent bioavailability of the non-sucralfate drugs without being absorbed or trapped by the sucralfate.

We claim:

1. A pharmaceutical preparation that contains sucralfate in the presence of another drug in such a way that the another drug is immediately released without being adsorbed on or trapped by the sucralfate, wherein the another drug is of such a nature that its absorption is interfered with by adsorption or trapping with the sucralfate.

2. A pharmaceutical preparation according to claim 1, wherein the sucralfate is contained separately from the another drug, said preparation consisting of an immediate release fraction containing the another drug and a delayed release fraction containing the sucralfate.

3. A pharmaceutical preparation according to claim 2, which is a bigranular mixture of an immediate release fraction of granules and a delayed release fraction of granules.

4. A two- or three-layered tablet according to claim 2, which comprises an immediate release layer and a delayed release layer.

5. A tablet according to claim 2, which comprises a delayed release core surrounded by an immediate release shell.

6. A pharmaceutical preparation according to claim 2, which comprises an immediate release matrix containing delayed release granules dispersed therein.

7. A pharmaceutical preparation according to claim 2, which is a tablet comprising a delayed release core entirely coated with an immediate release film of the another drug.

8. A pharmaceutical preparation according to claim 2, which is a granule comprising a delayed release core entirely coated with an immediate release film of the another drug.

9. A pharmaceutical preparation according to claim 2, which is a granule comprising a delayed release core entirely coated with an immediate release powder of the another drug.

10. A pharmaceutical preparation according to claim 2, which is a capsule filled with a mixture comprising a delayed release tablet, granule or powder combined with an immediate release tablet, granule or powder.

11. A pharmaceutical preparation according to claim 2, which is a solution or jelly having delayed release particles dispersed in an aqueous solution or jelly containing the another drug.

12. A pharmaceutical preparation according to claim 1, wherein said another drug is one member of the group consisting of: antiepileptics which are diazepam and phenytoin; antipyretics and analgesics which are acetaminophen, aspirin, ibuprofen, ketoprofen, naproxen and indomethacin; psychopharmacologic agents which are chlorpromazine hydrochloride, imipramine hydrochloride sulpiride; an antispasmodic drug which is methyl-benactyzium bromide; a cardiotonic which is digoxin; antidysrhythmic drugs which are procainamide hydrochloride, indenolol hydrochloride and verapamil hydrochloride; a diuretic which is furosemide; a hypotensive drug which is nicardipine hydrochloride; coronary vasodilators which are diltiazem hydrochloride, dipyridamole and nifedipine; a bronchodilator which is theophylline; $H_2$-receptor antagonists which are cimetidine, ranitidine, famotidine, nizatidine and loxatidine acetate; hormones which are prednisolone, ethynyl estradiol and warfarin potassium; an antidiabetic drug which is chlorpropamide; antibacterials which are aluminoparaaminosalicylic acid calcium salt, erythromycin, ciprofloxacin hydrochloride and norfloxacin; and combinations of these drugs.

13. A pharmacetical preparation according to claim 12, wherein said drug is a $H_2$-receptor antagonist selected from the group consisting of cimetidine, ranitidine, famotidine, nizatidine and loxatidine acetate.

* * * * *